United States Patent
Zemlok et al.

(10) Patent No.: US 8,591,396 B2
(45) Date of Patent: Nov. 26, 2013

(54) MAGNETIC GASTRIC REDUCTION DEVICE

(75) Inventors: Michael Zemlok, Prospect, CT (US); Adam Ross, Prospect, CT (US)

(73) Assignee: Covidien LP, Mansfield, MA (US)

( * ) Notice: Subject to any disclaimer, the term of this patent is extended or adjusted under 35 U.S.C. 154(b) by 277 days.

(21) Appl. No.: 12/758,853

(22) Filed: Apr. 13, 2010

(65) Prior Publication Data

US 2010/0280304 A1    Nov. 4, 2010

Related U.S. Application Data

(60) Provisional application No. 61/175,153, filed on May 4, 2009.

(51) Int. Cl.
*A61F 2/04*    (2013.01)

(52) U.S. Cl.
USPC .................. 600/37; 600/29; 600/30; 600/32

(58) Field of Classification Search
USPC .................. 600/29, 30, 32, 37; 128/897–899
See application file for complete search history.

(56) References Cited

U.S. PATENT DOCUMENTS

| | | | |
|---|---|---|---|
| 7,175,589 B2 | 2/2007 | Deem et al. | |
| 7,758,493 B2 | 7/2010 | Gingras | |
| 2002/0183768 A1 | 12/2002 | Deem et al. | |
| 2004/0089313 A1 | 5/2004 | Utley et al. | |
| 2004/0167583 A1 | 8/2004 | Knudson et al. | |
| 2004/0215159 A1* | 10/2004 | Forsell ........................... | 604/358 |
| 2004/0267291 A1 | 12/2004 | Byrum et al. | |
| 2005/0283235 A1 | 12/2005 | Kugler et al. | |
| 2006/0178555 A1 | 8/2006 | Bortolotti | |
| 2006/0235448 A1* | 10/2006 | Roslin et al. .................. | 606/157 |
| 2006/0247719 A1 | 11/2006 | Maschino et al. | |
| 2006/0247722 A1* | 11/2006 | Maschino et al. .............. | 607/40 |
| 2007/0027493 A1 | 2/2007 | Ben-Haim et al. | |
| 2007/0032807 A1 | 2/2007 | Ortiz et al. | |
| 2007/0093861 A1 | 4/2007 | Vardi | |
| 2007/0203511 A1 | 8/2007 | Vardi | |
| 2007/0239179 A1 | 10/2007 | Ortiz | |
| 2007/0265646 A1 | 11/2007 | McCoy et al. | |
| 2007/0276293 A1* | 11/2007 | Gertner ........................ | 600/593 |
| 2007/0276432 A1 | 11/2007 | Stack et al. | |
| 2007/0293878 A1 | 12/2007 | Butsch | |
| 2008/0172072 A1 | 7/2008 | Pool et al. | |

(Continued)

FOREIGN PATENT DOCUMENTS

WO    WO 2004/112563 A2    12/2004
WO    WO 2008/005387 A2    1/2008

(Continued)

OTHER PUBLICATIONS

European Search Report for EP 10250862.9-2310 date of completion is Jan. 24, 2011 (3 pages).

*Primary Examiner* — Christine Matthews
*Assistant Examiner* — Joshua D Lannu (57) ABSTRACT

A magnetic gastric reduction device includes magnetic elements adapted to couple to a stomach and a sensor adapted to detect stomach properties. The device also includes a control device operably coupled to the magnetic elements. The control device is adapted to operably communicate with the sensor and is configured to control the magnetic elements based on a property of the stomach detected by the sensor to cause the magnetic elements to selectively compress or decompress the stomach.

26 Claims, 6 Drawing Sheets

(56) References Cited

U.S. PATENT DOCUMENTS

| | | |
|---|---|---|
| 2008/0300618 A1 | 12/2008 | Gertner |
| 2009/0030475 A1* | 1/2009 | Brynelsen et al. ............... 607/40 |
| 2009/0240268 A1 | 9/2009 | Kassab et al. |
| 2009/0275961 A1 | 11/2009 | Harris et al. |
| 2009/0292160 A1* | 11/2009 | Nieman .......................... 600/16 |

FOREIGN PATENT DOCUMENTS

| | | |
|---|---|---|
| WO | WO 2008/091614 A1 | 7/2008 |
| WO | WO 2008/147582 A2 | 12/2008 |
| WO | WO 2008/150905 A1 | 12/2008 |

\* cited by examiner

MAGNETIC GASTRIC REDUCTION DEVICE

CROSS-REFERENCE TO RELATED APPLICATIONS

The present application claims priority to, and the benefit of, U.S. Provisional Application Ser. No. 61/175,153 filed May 4, 2009, the entire contents of which are hereby incorporated by reference.

BACKGROUND

1. Technical Field

The present disclosure relates to gastric reduction devices and, more particularly, to the use of magnetic devices to selectively adjust the capacity of the stomach.

2. Background of Related Art

To alleviate or improve morbid obesity, various bariatric procedures have been developed to reduce the volume of food that can be ingested within a particular time period. These procedures include various forms of stomach reduction, gastro-intestinal bypass and laparoscopic banding methods. While these known procedures are effective in the treatment of morbid obesity, the clinical implementation of devices for procedures such as laparoscopic banding, remains difficult. Further, once devices such as gastric bands are implemented, readjusting the device requires invasive procedures and manual readjusting.

SUMMARY

According to an embodiment of the present disclosure, a magnetic gastric reduction system includes magnetic elements adapted to couple to a stomach and a sensor adapted to detect stomach properties. The device also includes a control device operably coupled to the magnetic elements. The control device is adapted to operably communicate with the sensor and is configured to control the magnetic elements based on a property of the stomach detected by the sensor to cause the magnetic elements to selectively compress or decompress the stomach.

According to another embodiment of the present disclosure, a gastric suppression device includes one or more electrodes adapted to couple to a stomach and one or more sensors adapted to detect stomach properties. A control device is operably coupled to the one or more electrodes and is adapted to operably communicate with the one or more sensors. The control device is configured to control the one or more electrodes based on the stomach properties detected by the sensor to cause the one or more electrodes to selectively compress the stomach.

According to another embodiment of the present disclosure, a method of performing a gastric suppression procedure includes the steps of coupling one or more magnetic elements to a stomach and detecting one or more properties of the stomach. The method also includes the step of controlling the one or more magnetic elements to selectively suppress at least a portion of the stomach based on the one or more detected properties of the stomach.

BRIEF DESCRIPTION OF THE DRAWINGS

Embodiments of the presently disclosed gastric reduction device are disclosed herein with reference to the drawings wherein.

DETAILED DESCRIPTION OF THE EMBODIMENTS

Embodiments of the presently disclosed gastric reduction device will now be described in detail with reference to the drawings in which like reference numerals designate identical or corresponding element in each of the several views.

Throughout this description, the term "proximal" will refer to the portion of the device closest to the operator and the term "distal" will refer to the portion of the device furthest from the operator.

Figure 1:
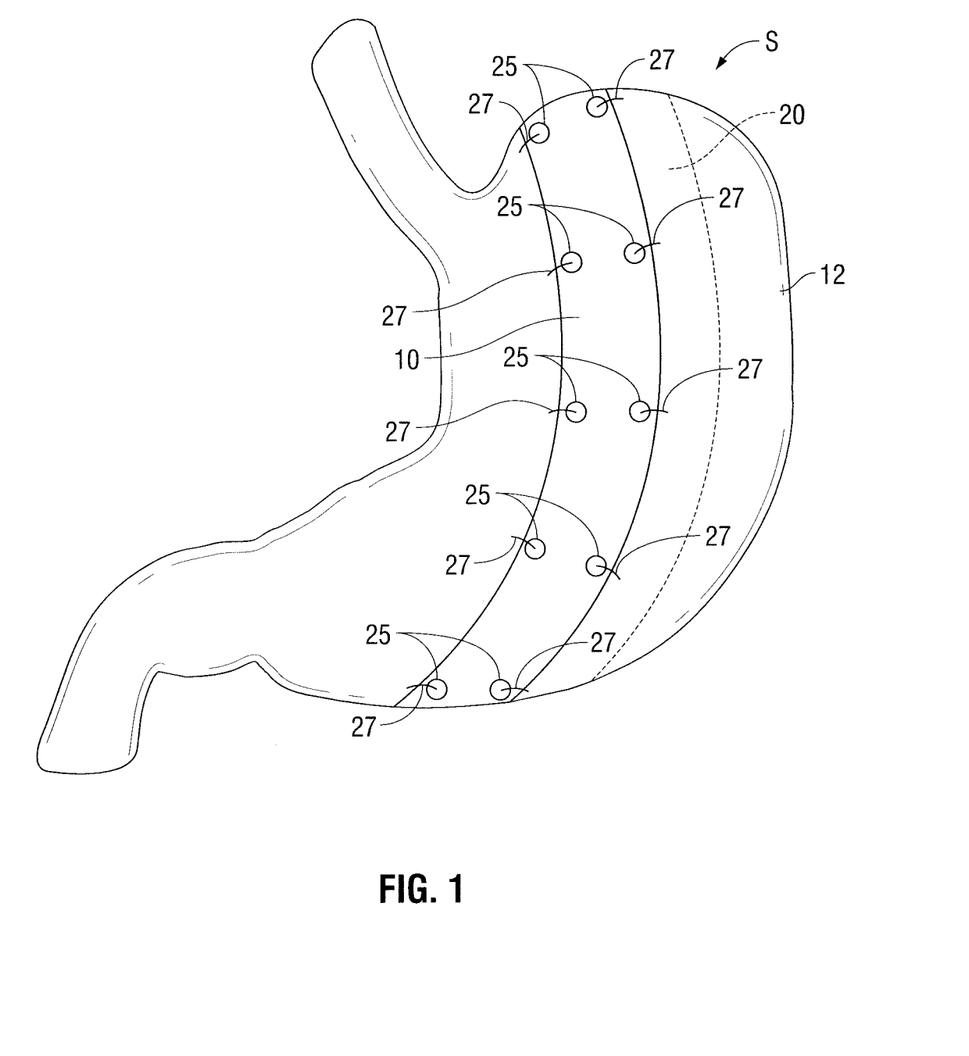
FIG. 1 is a schematic view of a magnetic gastric reduction device wrapped around a stomach in accordance with an embodiment of the present disclosure.

Referring to FIG. 1, a flexible magnetic strip 10 is shown attached to a portion 12 of a stomach "s". A second flexible magnetic strip 20 (shown in phantom) is attached to an opposing side of stomach "s" that mirrors portion 12 of stomach "s". The magnetic strips 10, 20 are kept in place relative to stomach "s" via suturing or other structures for fastening. More specifically, each of the strips 10, 20 include one or more anchor holes 25 defined therethrough. Each anchor hole 25 is adapted to receive a suture attachment 27 (e.g., staples, tacks, sutures) therethrough for securing the strips 10, 20 to the stomach "s". In use, strip 10 is magnetically attracted to strip 20, and vice-versa, such that a specific volume of the stomach may be selectively restricted or reduced, as discussed in further detail below.

In embodiments, each of magnetic strips 10, 20 may be formed from a magnetic sheet material. In other embodiments, magnetic strips 10, 20 may be formed from a matrix of magnets or inductive coils.

Figure 2:
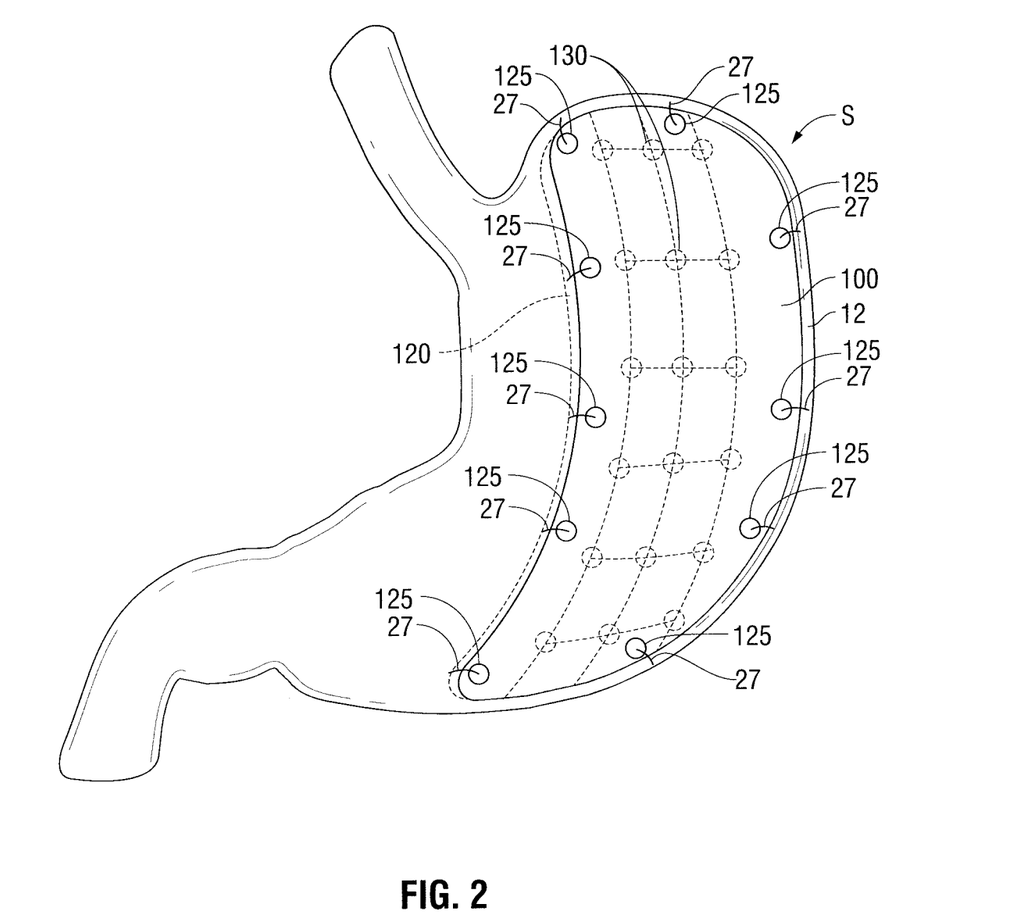
FIG. 2 is a schematic view of a magnetic gastric reduction device wrapped around a stomach in accordance with another embodiment of the present disclosure.

In another embodiment shown in FIG. 2, a flexible gastric pad 100 is shown attached to a portion 12 of stomach "s". A second pad 120 (shown in phantom) is attached to a corresponding portion (not shown) of stomach "s" that mirrors portion 12 of stomach "s". Pads 100, 120 are kept in place relative to stomach "s" via suturing or other fastening devices (e.g., staples, tacks, sutures). More specifically, each of the pads 100, 120 include one or more anchor holes 125 defined therethrough. Each anchor hole 125 is adapted to receive a suture attachment 27 therethrough for securing the pads 100, 120 to the stomach "s". In use, pad 100 is magnetically attracted to pad 120, and vice-versa, such that a specific volume of the stomach "s" may be selectively restricted or reduced, as discussed in further detail below.

In embodiments, magnetic pads 100, 120 may include a grid of magnetic elements 130, shown in phantom in the illustrated embodiment of FIG. 2. Magnetic elements 130 may be any combination of permanent magnets, electromagnets, and/or magnetic sheet materials. Magnetic elements 130 may be magnetized electronically or electromagnetically. More specifically, each magnetic element 130 may be magnetically adjusted in either manner discussed above independently or in unison with other magnetic elements 130 to contour the stomach "s" by reducing or restricting specific portions of the stomach "s".

Figure 3:
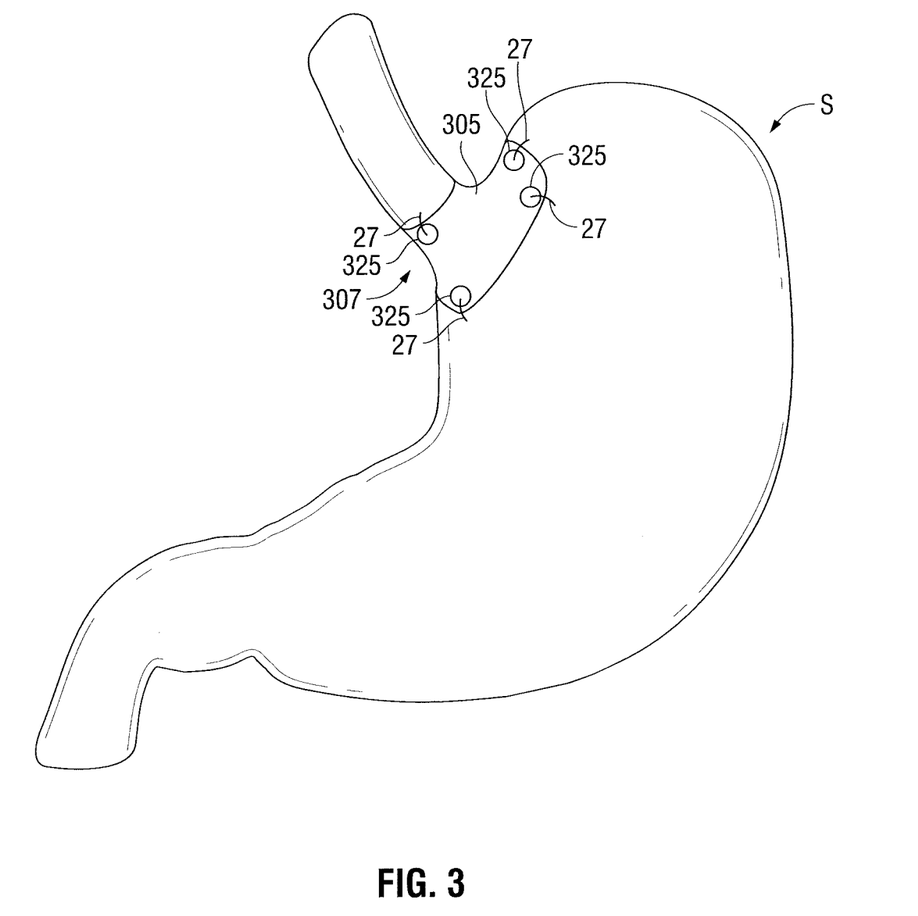
FIG. 3 is a schematic view of a magnetic gastric reduction device wrapped around a proximal portion of a stomach in accordance with another embodiment of the present disclosure.

In another embodiment shown in FIG. 3, a flexible band 305 is shown banded around a proximal pouch area 307 of a stomach "s". Band 305 is kept in place relative to proximal pouch area 307 via suturing or other fastening devices (e.g., staples, tacks, sutures). More specifically, band 305 includes one or more anchor holes 325 defined therethrough. Each anchor hole 325 is adapted to receive a suture attachment 27 therethrough for securing the band 305 to the proximal pouch 307 of stomach "s".

In embodiments, band 305 may be, for example, a grid of electromagnets, a grid of permanent magnets, and/or a sheet of magnetic materials. Band 305 may be magnetized electronically or electromagnetically. In use, the band 305 is magnetized to adjust band 305 such that a specific volume of the stomach "s" may be selectively restricted or reduced, as discussed in further detail below.

Figure 4:
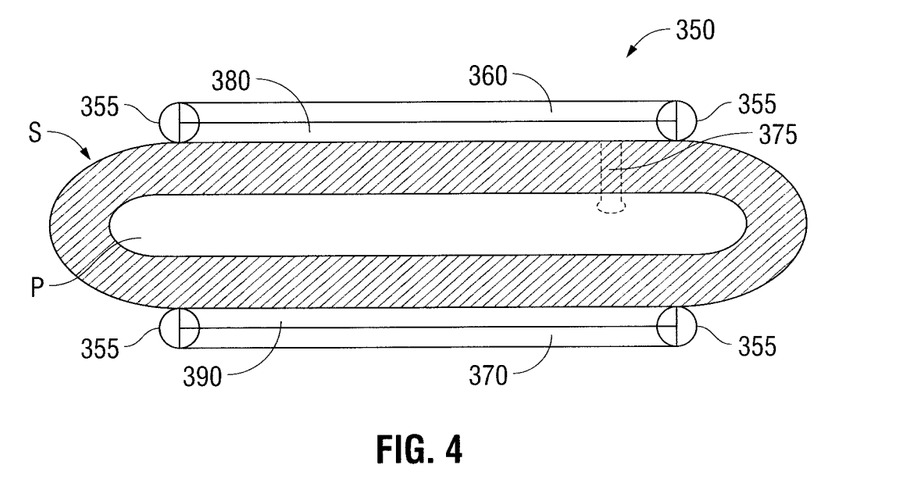
FIG. 4 is a cross-sectional view of a magnetic gastric reduction device wrapped around a stomach in accordance with another embodiment of the present disclosure.

FIG. 4 shows a cross-section of a stomach "s" having a gastric reduction device 350 attached thereto. Gastric reduction device 350 includes a pair of magnetic reduction elements 360 and 370 disposed on opposing sides of stomach "s". Elements 360 and 370 may be, for example, a pair of flexible gastric strips (FIG. 1), a pair of flexible gastric pads (FIG. 2), or a band (FIG. 3). Additionally or alternatively, elements 360, 370 may be formed as a magnetic reduction matrix (FIGS. 5 and 6) that at least partially encompasses stomach "s", as will be discussed in further detail below. In the illustrated embodiment, a pair of sensor layers 380 and 390 are disposed between elements 360 and 370, respectively, and an outer surface of the stomach "s". Sensor layers 380 and 390 are adapted to monitor pressure on the stomach, pulse oximetry, tissue oximetry, tissue vitality and/or tissue resiliency. In embodiments, sensor layers 380 and 390 may be formed as part of elements 360 and 370. Elements 360 and 370 are kept in place relative to stomach "s" via suturing. More specifically, elements 360, 370 may include one or more anchor holes (not shown) defined therethrough. Each anchor hole is adapted to receive a suture attachment 355 (e.g., staples, tacks, sutures) therethrough for securing gastric reduction device 350 and sensor layers 380, 390 to an outer surface of the stomach "s".

A sensor probe 375 may extend from sensor layer 380 and/or 390 through the surface of the stomach "s". The sensor probe 375 is adapted to sense gastric secretions inside a pocket "p" of the stomach "s". As best shown in FIG. 4, the pocket "p" of stomach "s" is a volume defined within the outer periphery of the stomach "s" that changes in accordance with the pressure applied by gastric reduction device 350 on stomach "s".

Figure 5:
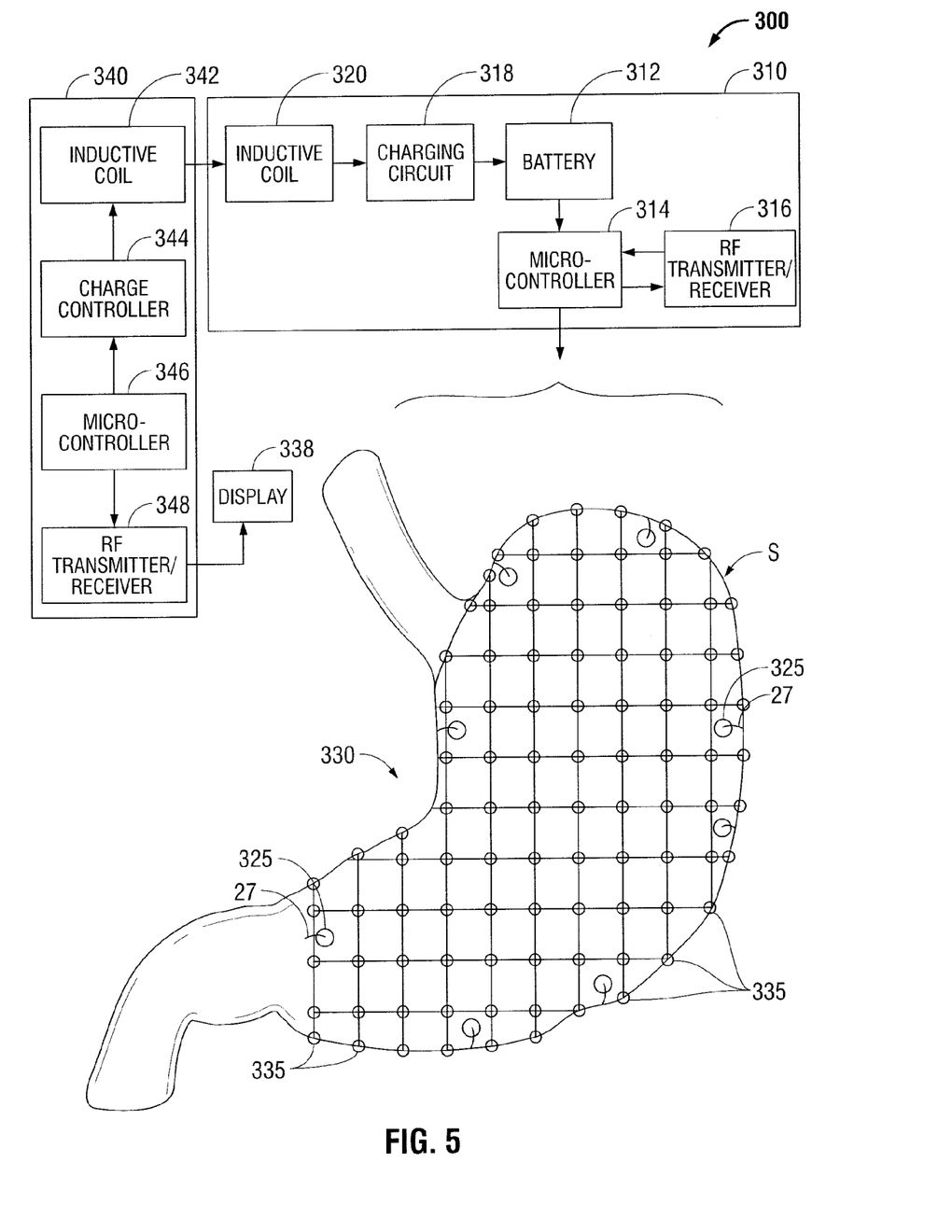
FIG. 5 is a schematic view of a gastric reduction control system in accordance with an embodiment of the present disclosure.

In another embodiment shown in FIG. 5, a gastric reduction control system 300 includes a magnetic reduction matrix 330 adapted to that at least partially encompass a stomach "s". Matrix 330 is operably coupled to an implantable control device 310. Implantable control device 310 is adapted to communicate with an external control device 340 to facilitate control of the magnetic reduction matrix 330 to adjust the pressure on the stomach "s" or, more specifically, restrict a specific volume of the stomach "s". As illustrated in FIG. 5, magnetic reduction matrix 330 is embodied as a grid of magnetic elements 335. In other embodiments, magnetic reduction matrix 330 may be incorporated within, for example without limitation, a flexible gastric strip (FIG. 1), a flexible gastric pad (FIG. 2), or a flexible band (FIG. 3). In the illustrated embodiment, magnetic reduction matrix 330 is comprised of magnetic elements 335 in a grid-like configuration. Elements 335 may be, for example, electromagnets, permanent magnets, permanent magnetic sheet material, neurostimulating electrodes, suppression-type electrodes, or any combination thereof.

External control device 340 is adapted to operate external to a patient and operably communicate with implantable control device 310. External control device 340 includes an inductive coil 342, a charge controller 344, a microcontroller 346, and an RF transmitter/receiver 348. External control device 340 may be coupled to a suitable power source (e.g., AC line voltage, a battery, etc.) to provide power to microcontroller 346, charge controller 344, RF transmitter/receiver 348, and inductive coil 342. External control device 340 is adapted to operably communicate via RF transmitter/receiver 348 with a display device 338 adapted to display sensory data, as will be discussed in further detail below.

Implantable control device 310 is implanted within the patient and may be affixed to magnetic reduction matrix 330 or, alternatively, may be disposed within magnetic reduction matrix 330. Implantable control device 310 includes a battery 312, a microcontroller 314, an R.F. transmitter/receiver 316, a charging circuit 318, and an inductive coil 320. The microcontroller 314 and RF transmitter/receiver 316 are powered by the battery 312. The battery 312 is, in turn, charged by the inductive coil 320 via the charging circuit 318.

Using electrical current generated by a suitable power source, inductive coil 342 of external control device 340 generates an electromagnetic field from which inductive coil 320 of implantable control device 310 wirelessly draws energy. Inductive coil 320 converts the energy drawn from inductive coil 342 back into electrical current and charging circuit 318 charges the battery 312 with the converted electrical current. In this manner, no electrical leads or conductors from the implantable control device 310 to the external control device 340 are necessary to charge the battery 312. That is, no electrical leads or conductors from implantable control device 310 and/or magnetic reduction device 330 are external relative to the patient. As such, battery 312 may be charged non-conductively from a source (i.e., external control device 340) external to the patient.

As discussed above, battery 312 powers microcontroller 314 and RF transmitter/receiver 316. The microcontroller 314 is interfaced with the magnetic reduction device 330 and various sensors associated therewith such as, for example, sensor probe 375 and sensor layers 380, 390 (FIG. 4). Based on sensory feedback from the sensors and/or clinician feedback, the microcontroller 314 adjusts the magnetic reduction device 330 by magnetizing or demagnetizing any one or more magnetic elements 335 to adjust the pressure applied by the magnetic reduction device 330 on the stomach "s". More specifically, the microcontroller 314 may alter the voltage supplied to each magnetic element 335, thereby altering the magnetic field strength of specific elements 335 and/or specific rows or sections of elements 335, which, in turn, increases or decreases the attraction between opposing elements 335, opposing rows of elements 335, and/or opposing sections of elements 335.

Sensory data from the sensors (e.g., sensor probe 375, sensor layers 380, 390) may be transmitted from implantable control device 310 via RF transmitter/receiver 316 for subsequent storage and/or clinical review. Further, based on the transmitted sensory data, system adjustments, system status, and/or battery status may be determined. For example, RF transmitter/receiver 348 of external control device 340 may be adapted to communicate with RF transmitter/receiver 316 of implantable control device 310 to receive sensory data therefrom. RF transmitter/receiver 348 is adapted to transmit the received sensory data to the display device 338. The display device 338, in turn, enables clinicians to analyze the sensory data. Further, clinicians may communicate system settings and/or software updates (i.e., via RF transmitter/receiver 348 or any suitable transmitting device) to microcontroller 314 of implantable control device 310 through RF transmitter/receiver 316.

Sensory data received by RF transmitter/receiver 348 that is specific to the status of battery 312 (e.g., battery level, battery condition, etc.) may be utilized by microcontroller 346 to conduct electrical current (e.g., from a suitable power source) to inductive coil 342, as discussed herein above. The amount of electrical current conducted to inductive coil 342 is controlled by charge controller 344 in accordance with the needs of battery 312 as indicated via the sensory data. As discussed hereinabove, utilizing the electrical current, inductive coil 342 generates an electromagnetic field from which inductive coil 320 of implantable control device 310 wirelessly draws energy.

In embodiments, microcontroller 314 of implantable control device 310 may operate in any one of various modes of operation to control the matrix 330. For example, based on sensory feedback from the sensors and/or clinician feedback, microcontroller 314 may compress a specific volume of stomach "s" when sensory feedback indicates that the patient is hungry or eating (e.g., based on sensed gastric secretions). In this scenario, microcontroller 314 may minimize the amount of time that stomach "s" is compressed or restricted to allow for the intake of food. In another scenario, if sensors or a clinician detect an illness, pregnancy, and/or consistent altered eating habits, microcontroller 314 or the clinician may terminate operation of gastric reduction control system 300 until subsequent reactivation once sufficient health of the patient is determined by the sensors or the clinician.

In embodiments, system 300 may incorporate a timer to compress the stomach "s" for predetermined time periods and/or a specific time of the day.

In other embodiments, system 300 or, more particularly microcontroller 314, may include a voice recognition software application adapted to process voice commands from the patient and/or the clinician to selectively control the matrix 330.

Figure 6:
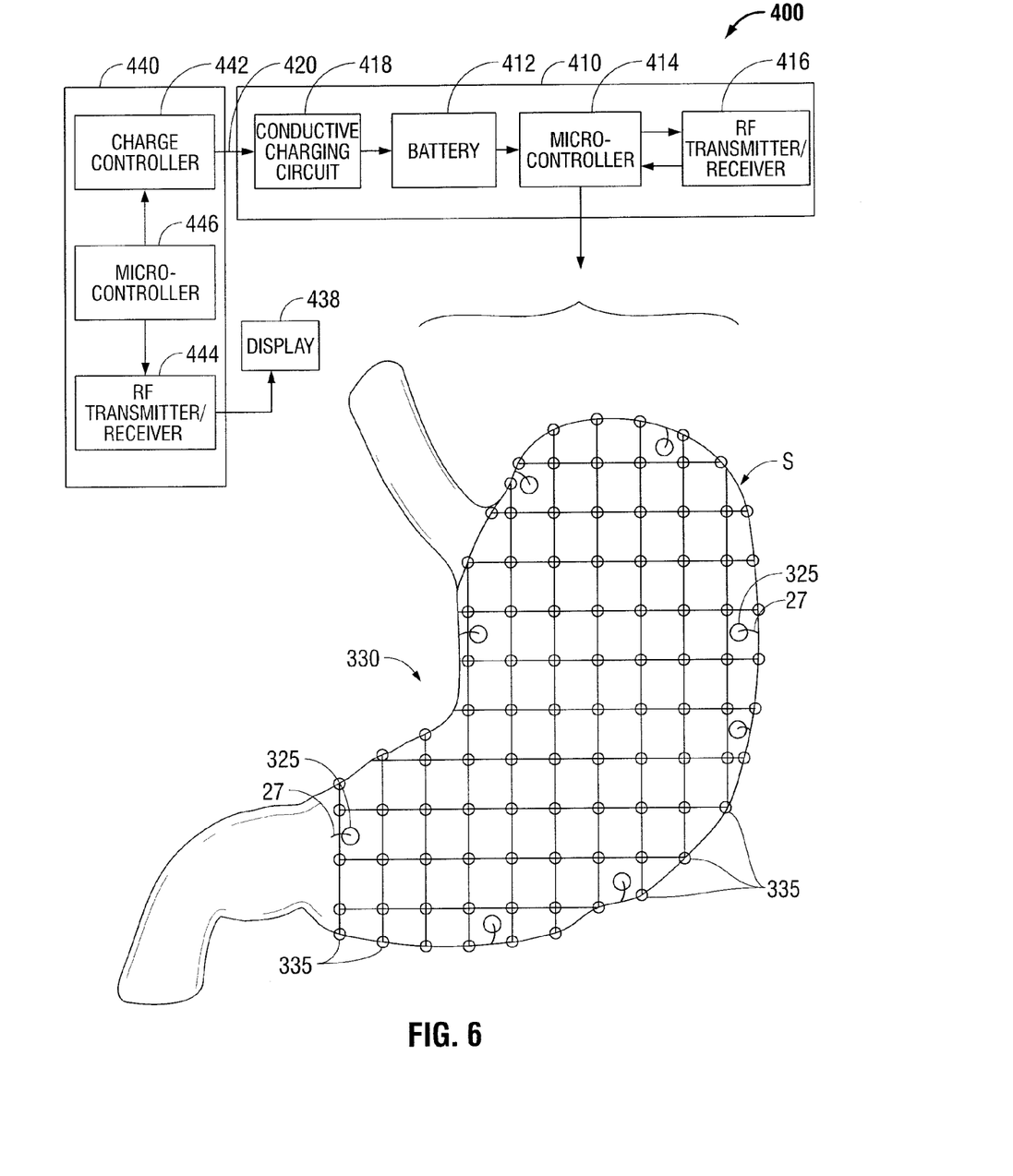
FIG. 6 is a schematic view of a gastric reduction control system in accordance with another embodiment of the present disclosure.

In another embodiment shown in FIG. 6, a gastric reduction control system 400 includes a magnetic reduction matrix 430 that is adapted to at least partially encompass a stomach "s". Matrix 430 is operably coupled to an implantable control device 410. Implantable control device 410 is adapted to communicate with an external control device 440 to facilitate control of the magnetic reduction matrix 430 to adjust the pressure on the stomach "s" or, more specifically, restrict a specific volume of the stomach "s". As illustrated in FIG. 6, magnetic reduction matrix 430 is embodied as a grid of magnetic elements 460 (e.g., permanent magnets, electromagnets, etc.). Gastric reduction control system 400 is substantially as described above with respect to gastric reduction control system 300 of FIG. 5 and will only be described to the extent necessary to explain its difference.

External control device 440 is adapted to operate external to a patient and operably communicate with implantable control device 410. External control device 440 includes a charge controller 442, a microcontroller 446, and an RF transmitter/receiver 444. External control device 440 may be coupled to a suitable power source (e.g., AC line voltage, a battery) to provide power to microcontroller 446, charge controller 444, and RF transmitter/receiver 448. External control device 440 is adapted to operably communicate via RF transmitter/receiver 444 with a display device 438 adapted to display sensory data, as will be discussed in further detail below.

Implantable control device 410 is implanted within the patient and may be affixed to magnetic reduction matrix 430 or, alternatively, may be disposed within magnetic reduction matrix 430. Implantable control device 410 includes a battery 412, a microcontroller 414, an R.F. transmitter/receiver 416, and a conductive charging circuit 418. The conductive charging circuit 418 includes an electrical lead 420 adapted to extend from implantable control device 410 and externally from the patient. Electrical lead 420 is adapted to connect conductive charging circuit 418 to external control device 440, as will be discussed in further detail below. The microcontroller 414 and RF transmitter/receiver 416 are powered by the battery 412. The battery 412, in turn, is charged by the conductive charging circuit 418. More specifically, the charge controller 442 regulates electrical current from the external control device 440 to the conductive charging circuit 418 based on sensory feedback from sensors (e.g., sensor probe 375, sensor layers 380, 390) and/or clinician feedback. Conductive charging circuit 418 conductively charges the battery 412 with the electrical current from external control device 440 and/or a suitable power source operably coupled thereto.

As discussed above, battery 412 powers microcontroller 414 and RF transmitter/receiver 416. The microcontroller 414 is interfaced with the magnetic reduction device 330 and various sensors (e.g., sensor layers 380 and 390) associated therewith. Based on sensory feedback from the sensors and/or clinician feedback, the microcontroller 414 adjusts the magnetic reduction device 430 by magnetizing or demagnetizing any one or more magnetic elements 460 to adjust the pressure applied by magnetic reduction device 430 on the stomach "s".

As described above with respect to magnetic reduction device 330 of FIG. 5, sensory data from the sensors (e.g., sensor probe 375, sensor layers 380, 390) may be transmitted from implantable control device 410 via RF transmitter/receiver 416 for subsequent storage and/or clinical review (e.g., via display 438).

For any one of the above described embodiments, an MRI or CAT scan may be taken of the abdomen of a patient to determine geometry and/or dimensions specific to the stomach of that patient. Based on this information, custom alterations may be made to conform a magnetic reduction device to the contours of a stomach prior to implementation.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. A magnetic gastric reduction device, comprising:
    a grid of magnetic elements configured to circumferentially encompass a stomach such that at least two magnetic elements of the grid are arranged to magnetically attract through the stomach to selectively compress the stomach therebetween;
    at least one sensor adapted to detect at least one property of the stomach; and
    a control device operably coupled to the grid of magnetic elements and adapted to operably communicate with the at least one sensor, the control device configured to control a voltage supplied to each magnetic element of the grid independently based on at least one property of the stomach detected by the sensor to adjust magnetic attraction of the each magnetic element relative to at least one other magnetic element of the grid to selectively compress the stomach.

2. A magnetic gastric reduction device according to claim 1, wherein the control device includes an internal device configured to be implanted within a patient and an external device disposed external to the patient and adapted to communicate with the internal device.

3. A magnetic gastric reduction device according to claim 1, wherein the grid of magnetic elements is a flexible magnetic strip configured to be coupled to opposing portions of the stomach.

4. A magnetic gastric reduction device according to claim 1, wherein the grid of magnetic elements is a matrix of magnets configured to at least partially encompass the stomach.

5. A magnetic gastric reduction device according to claim 1, wherein the grid of magnetic elements is a flexible pad configured to at least partially encompass the stomach.

6. A magnetic gastric reduction device according to claim 1, wherein the grid of magnetic elements is a flexible band configured to be coupled to a proximal pouch area of the stomach.

7. A magnetic gastric reduction device according to claim 1, wherein the grid of magnetic elements is configured to be selectively magnetized by the control device.

8. A magnetic gastric reduction device according to claim 1, wherein the grid of magnetic elements is configured to be sutured to the stomach.

9. A magnetic gastric reduction device according to claim 1, wherein the grid of magnetic elements includes at least two magnetic elements configured to be disposed on opposing portions of the stomach and configured to magnetically attract to each other.

10. A magnetic gastric reduction device according to claim 1, wherein the grid of magnetic elements is selected from the group consisting of an electromagnet, a permanent magnet, a magnetic sheet material, a neuro-stimulating electrode, and a suppression-type electrode.

11. A magnetic gastric reduction device according to claim 1, wherein the at least one sensor is configured to be disposed on an outer surface of the stomach and adapted to detect at least one of stomach pressure, stomach pulse oximetry, stomach tissue oximetry, stomach tissue vitality, and stomach tissue resiliency.

12. A magnetic gastric reduction device according to claim 1, wherein the at least one sensor includes a probe configured to extend into a pocket of the stomach, the probe adapted to sense gastric secretions within the pocket.

13. A magnetic gastric reduction device according to claim 1, wherein the control device is configured to adjust the magnetization of a first plurality of magnetic elements of the grid relative to a second plurality of magnetic elements of the grid disposed on an opposing side of the stomach to selectively compress at least a portion of the stomach.

14. A gastric suppression device, comprising:
a grid of electrodes configured to circumferentially encompass a stomach such that at least two electrodes of the grid are arranged to magnetically attract through the stomach to selectively compress the stomach therebetween;
at least one sensor adapted to detect at least one property of the stomach; and
a control device operably coupled to the grid of electrodes and adapted to operably communicate with the at least one sensor, the control device configured to control a voltage supplied to each electrode of the grid independently based on the at least one property of the stomach detected by the sensor to adjust magnetic attraction of each electrode relative to at least one other electrode of the grid to selectively compress the stomach.

15. The gastric suppression device according to claim 14, wherein the grid of electrodes includes at least one of a neuro-stimulating type electrode and a suppression-type electrode.

16. A method of performing a gastric suppression procedure, comprising the steps of:
circumferentially encompassing a stomach with a grid of magnetic elements such that at least two magnetic elements of the grid magnetically attract through the stomach to selectively compress the stomach therebetween;
detecting at least one property of the stomach; and
controlling a voltage supplied to each magnetic element of the grid independently to adjust magnetic attraction of each magnetic element of the grid relative to at least one other magnetic element of the grid to selectively compress at least a portion of the stomach based on the at least one detected property of the stomach.

17. The method according to claim 16, wherein the controlling step further includes one of magnetizing and demagnetizing at least one magnetic element of the grid.

18. The method according to claim 16, wherein the at least one property of the stomach is selected from the group consisting of pressure, pulse oximetry, tissue oximetry, tissue vitality, and tissue resiliency.

19. The method according to claim 16, wherein the detecting step further includes sensing gastric secretions within a pocket of the stomach.

20. The method according to claim 16, further comprising a coupling step wherein the coupling step further includes suturing the grid of magnetic elements to at least a portion of the stomach.

21. The method according to claim 16, wherein the controlling step further includes selectively suppressing a proximal pouch portion of the stomach.

22. The method according to claim 16, wherein the controlling step further includes adjusting the magnetization of a first plurality of magnetic elements of the grid relative to a second plurality of magnetic elements of the grid disposed on an opposing side of the stomach to selectively compress at least a portion of the stomach.

23. A magnetic gastric reduction system, comprising:
a grid of magnetic elements configured to circumferentially encompass a stomach such that at least two magnetic elements of the grid are arranged to magnetically attract through the stomach to selectively compress the stomach therebetween;
at least one sensor adapted to detect at least one property of the stomach; and
a control device operably coupled to at least one magnetic element of the grid of magnetic elements and adapted to operably communicate with the at least one sensor, the control device including an interior controller configured to be implanted within a patient to control a voltage supplied to each magnetic element independently to adjust magnetization of each magnetic element based on at least one property of the stomach detected by the sensor and an exterior controller configured to communicate with the interior controller from an exterior of the patient; and
a power source disposed on the interior controller and configured to provide power thereto, the exterior controller configured to inductively provide energy to the interior controller to charge the power source.

24. A magnetic gastric reduction system according to claim 23, wherein the interior controller includes an inductive element configured to draw energy from the exterior controller to provide energy to the power source.

25. A magnetic gastric reduction system according to claim 24, wherein the inductive element is configured to provide energy to a charging circuit disposed on the interior controller, the charging circuit configured to charge the power source.

26. A magnetic gastric reduction system according to claim 24, wherein the exterior controller includes an inductive element configured to generate a magnetic field from which the inductive element of the interior controller draws energy.

* * * * *